US011521723B2

(12) United States Patent
Liu et al.

(10) Patent No.: US 11,521,723 B2
(45) Date of Patent: Dec. 6, 2022

(54) USING NATURAL LANGUAGE PROCESSING TO FIND ADVERSE EVENTS

(71) Applicant: Abiomed, Inc., Danvers, MA (US)

(72) Inventors: Chen Liu, Danvers, MA (US); Ahmad El Katerji, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 289 days.

(21) Appl. No.: 16/722,303

(22) Filed: Dec. 20, 2019

(65) Prior Publication Data

US 2020/0202990 A1 Jun. 25, 2020

Related U.S. Application Data

(60) Provisional application No. 62/784,192, filed on Dec. 21, 2018.

(51) Int. Cl.
*G16H 15/00* (2018.01)
*G16H 40/40* (2018.01)
*G06F 40/284* (2020.01)
*G06F 40/30* (2020.01)

(52) U.S. Cl.
CPC ........... *G16H 15/00* (2018.01); *G06F 40/284* (2020.01); *G06F 40/30* (2020.01); *G16H 40/40* (2018.01)

(58) Field of Classification Search
None
See application file for complete search history.

(56) References Cited

U.S. PATENT DOCUMENTS

2002/0083080 A1* 6/2002 Classen ................. G06F 16/284

OTHER PUBLICATIONS

Harpaz, Rave et al. "Text mining for adverse drug events: the promise, challenges, and state of the art." Drug safety vol. 37,10 (2014): 777-90. doi:10.1007/s40264-014-0218-z (Year: 2015).*
Sankey, Embase Seminar, Elsevier, Sep. 14, 2016, https://www.kcgg.ugent.be/wordpress/wp-content/uploads/2016.09.14-Presentatie-Embase_Ros.pdf (Year: 2016).*

(Continued)

*Primary Examiner* — Devin C Hein
(74) *Attorney, Agent, or Firm* — Botos Churchill IP Law LLP (57) ABSTRACT

A method for automatically classifying clinical descriptions of patients by a computer processor using natural language processing is provided. The clinical descriptions relate to the use of a ventricular assist device to treat the patient. The method comprises receiving at least one clinical description comprising text. The method also then comprises determining the position of a target word within the text. Further the method comprises determining the existence of at least one negation word within an active region, the active region comprising a predetermined number of words within the text occurring immediately before and immediately after the target word, including the target word. The method then comprises determining the existence of at least one body-part word within the active region. Lastly, the method comprises determining that the clinical description is to be disregarded if the active region contains either a negation word or a body-part word.

18 Claims, 6 Drawing Sheets

(56) References Cited

OTHER PUBLICATIONS

Chapman WW, Bridewell W, Hanbury P, Cooper GF, Buchanan BG. A simple algorithm for identifying negated findings and diseases in discharge summaries. J Biomed Inform. Oct. 2001;34(5):301-10. doi: 10.1006/jbin.2001.1029. PMID: 12123149. (Year: 2001).*

Acharya, Deepak et al. "Ventricular Assist Device in Acute Myocardial Infarction." Journal of the American College of Cardiology vol. 67,16 (2016): 1871-80. doi:10.1016/j.jacc.2016.02.025 (Year: 2016).*

International Preliminary Report on Patentability dated Jun. 16, 2021 for International Application No. PCT/US2019/067741 and Written Opinion and International Search Report dated Apr. 1, 2020 (12 pp).

Manana Khachidze et al, "Natural Language Processing Based Instrument for Classification of Free Text Medical Records", Biomed Research International, vol. 2016, Jan. 1, 2016, (pp. 1-10).

Shu Dong et al, "Using Natural Language Processing to Screen Patients with Active Heart Failure, An Exploration for Hospital-wide Surveillance", Sep. 6, 2016, Ret. from the Internet: URL:https://arxiv.org/ftp/arxiv/papers/1609/1609.01580.pdf, (8 pp).

* cited by examiner

Description: Pt presented after 5 days of active chest pain and
SOB. subtotal LAD/CTO CIRC/ CTO RCA. Dr Pershad placed Impella
immediately knowing pt would not tolerate extensive revasc.
PTCA and stented all lesions- during RCA fix pt lost
pulsatitlity, but was still talking with staff. Completed
revasc without any complications. double percales technique
completed without complications and no bleeding ~510

520 ⌐        ⌐ 530
FIG. 5A                           500

Description: Cardiac Arrest patient with history of heart
failure and CABG. Currently on Neo, Levo and unconfirmed amount
of Epi. Patient was down and CPR performed by EMT and bystander
prior to EMT arrival. Patient is awake and alert although
intubated. Patient is on P6 with flows of 2.6 L/min. little
difference in flows between P6 and P8 as patient is fairly
constricted peripherally. Plan to wean Epi and Levo as soon as
possible. Waiting for central line or Swan to be placed for
assessment. He is currently getting volume at around 300 per
hour. Watching output and have discussed potentially giving
Lasix but will watch volume status for Impella. Have given
bolus of 500 for volume after echo. Pressure is 91/76/80. PP is
602. purge flow is 11.2. MC at 619/489/546. groin site is dry
with no evidence of bleeding at all. 10-24 parameters remain
steady. Dialysis was started this morning at 7 am. MAP in the
70's with narrow pulse pressure. Patient is still alert and
aware but lightly sedated. Patient passed last night 580    560                       570
FIG. 5B                              550

Description: Pt was a pericardial window and crumped. Impella placed. PMH:Hypothyyroidism due to resection due to thyroid cancer, HTN, CAD, kidney transplant, scoliosis.Initally placed independent and arrived onsite for unit management. on p4 flow 1.4-very small in size individual. PS; 116/80(95), MC: 502/ 288(281), PP: 502, PIF: D5 with 6250 hep at 11.2. Gtts: Dopa 10, Levo 30. Issue now is distended abdomen and multiple foley attempts-no urine output as of yet. 11/24 Called several times for an update. Nurse is very busy, she will call the 800# with the update when she gets a chance. MA 11/25 CSC PM Update Pt is very sick and they feel she is bleeding into her abdomen. Pt is off all Heparin. P/IF 8/1.4 PS 121/74 MC 542/340 PP/PF 480/12.2 UOP- Zero Gtts: Epi and Levo Going to get multiple blood products tonight. . Pt is in sinus tach- rate of 140. Plan is to explant tomorrow and insert Quintron catheter for dialysis. Pt is in Liver failure. Will call the 800# with any issues. MA 11/26 CSC PM update: Spoke with charge RN who reported the Impella was removed and the patient is currently stable. Date/ time of explant and outcome edited. RD

FIG. 6A

Description: Pt presented to ER acute MI and emergently brought to Cath labSuccessful PCI with 3 stents to cfx, 3 stents to Lad, and 1 to left main. Somewhat stable. Having left groin bleed so Integrelin placed on hold. No systemic heparin for now. ACT 110-120. To eval this AM for restarting. Nurse made aware need for anticoagulation and pump protection. Does have D5 with 6250 Heparin in purge. Has lost placement signal despite attempt to aspirate back. Remote link up and running. Nurse comfortable with Impella. 1/11 CSC PM Update: Spoke with Cindy Impella removed at 6pm and pt doing well. Will update case with date, time and outcome. MA

FIG. 6B

USING NATURAL LANGUAGE PROCESSING TO FIND ADVERSE EVENTS

CROSS-REFERENCE TO RELATED APPLICATION

This application claims the benefit of U.S. Provisional Patent Application No. 62/784,192, filed Dec. 21, 2018. The disclosure of the foregoing application is incorporated herein by reference in its entirety.

BACKGROUND

Cardiovascular conditions can reduce the quality of life of a patient. A variety of treatment options have been developed for treatment of the heart in such conditions, ranging from pharmaceuticals to mechanical devices and transplantation. Ventricular assist devices (VADs), such as heart pump systems and catheter systems, are often used in treatment of the heart to provide hemodynamic support and facilitate recovery. Some heart pump systems are percutaneously inserted into the heart and can run in parallel with the native heart to supplement cardiac output. Such heart pump systems include the Impella® family of devices by Abiomed, Inc. of Danvers, Mass. Some of these medical procedures may lead to adverse events occurring in the patient during treatment. This may be due to incorrect use of the device, or sub-optimal device configurations.

After administering a treatment to a patient using a medical device, such as a VAD, a detailed description of the treatment provided to the patient, and any clinical indications during such treatment, is recorded. Such recordation has traditionally been done in writing manually in clinical short hand or typed into a computer. Alternatively, details of the treatment are provided to a device which converts speech to text (e.g. a dictaphone, or a laptop microphone with speech recognition software running thereon) and is stored as a text file. Such files are often logged in a patient data repository and made available to other clinicians requiring access to the patient's medical file.

Usually clinicians have to determine if a patient has experienced an adverse event during treatment before deciding on any further treatment. Adverse events include, for example, bleeding, hemolysis and ischemia, that may have occurred during the use of a VAD to treat the patient (due to use of a new guidewire with an Impella® pump, for example). Such determination involves reading and inspecting clinical records to manually ascertain if any such adverse events have occurred during the treatment. Manual inspection involves several degrees of freedom. For example, certain portions of the text of a clinical description may be missed or be difficult to decipher, or the interpretation of a clinical description may vary from person to person. Further, to obtain clinical indicia of a treatment plan (e.g. success rate), a repository of clinical descriptions need to be analyzed so as to obtain indices that are representative. Manual inspection of large numbers of clinical descriptions will take time and may involve several inaccuracies due to the aforementioned degrees of freedom.

Attempts to automate the analysis of clinical descriptions involve the use of natural language pre-processing and machine learning, such as bagging and random forest, logistic regression, and regression tree, for example. Such algorithms are complex and recursive, and take up processor resources on a computing system especially when the algorithms do not converge easily. Machine learning using such algorithms also often require a sizable pool of training data before the machine model can be relied on. Thus for smaller data repositories, insufficient training data will result in unstable machine learning models, the output of which will be unreliable in analyzing clinical descriptions.

SUMMARY

The methods and systems described herein use natural language processing and keyword searching by a processor of a computing apparatus to determine if a clinical description relates to a treatment that contains an adverse event. The method beings by receiving at least one clinical description comprising text. The processor then determines the position of a target word within the text. The processor then progresses to determine the existence of at least one negation word within an active region, the active region comprising a predetermined number of words within the text occurring immediately before and immediately after the target word, including the target word. Next the processor determines the existence of at least one body-part word within the active region. The method then determines that the clinical description is to be disregarded if the active region contains either a negation word or a body-part word.

By searching for a keyword in the text of a clinical description, training of a machine learning algorithm (involving training data) is not required, thereby freeing up system resources of a computing apparatus. The keyword search nature of the method and system of the present disclosure does not monopolize the processor of a computing apparatus performing the analysis of the clinical descriptions.

In some implementations, the method further comprises processing the text to generate word tokens, determining and grouping word tokens comprising inflected forms of a word, and performing a keyword search on the text using the grouped word tokens. In other implementations, the method comprises flagging the clinical description if the active region does not contain: a negation word and a body-part word. In certain implementations, the method comprises writing a flag to a header in the clinical description. In some implementations, the predetermined number of words of the active regions is at least three words. In other implementations, the predetermined number of words of the active regions is three. In certain implementations, the at least one negation word comprises any one of: 'no', 'not', 'nor', 'non', 'without', 'never', and 'false'. In some implementations, the clinical descriptions are obtained from an Acute Myocardial Infarction Cardiogenic Shock (AMICS) repository.

In another embodiment, there is provided a system for automatically classifying clinical descriptions of patients. The system comprises at least one ventricular assist device (VAD) for treating a patient. The system also comprises a controller in communication with the VAD and configured to generate at least one clinical description of the treatment of the patient with the VAD. Further the system comprises a data repository for storing the clinical description of the treatment. The system also comprises a processor in communication with the data repository, the processor configured to perform the method according to any of the aforementioned embodiments. In some implementations, the system disables the use of a VAD if the number of clinical descriptions containing adverse events exceeds a predetermined threshold.

In yet another embodiment, there is provided a system for automatically classifying clinical descriptions of patients, each clinical description relating to the use of a ventricular assist device on the patient. The system comprises a processor configured to perform the method according to any of the aforementioned embodiments.

In a further embodiment, there is provided a computer program comprising computer executable instructions, which, when executed by a computing apparatus comprising a processor, causes the computing apparatus to perform a method according to any of the aforementioned embodiments.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIGS. 6A and 6B illustrate the use of the method of FIG. 1 on a clinical description containing a body-part word.

DETAILED DESCRIPTION

To provide an overall understanding of the methods and systems described herein, certain illustrative embodiments will be described. Although the embodiments and features described herein are specifically described for use in connection with using natural language processing to automatically detect adverse events in clinical description involving the use of ventricular assist devices (VADs), it will be understood that all the components and other features outlined below may be combined with one another in any suitable manner and may be adapted and applied to other types of medical therapy having clinical descriptions associated therewith.

The systems and methods described herein use natural language processing (NLP) to automatically detect the occurrence of adverse events in clinical descriptions. NLP is used to perform a search for keywords in an active region of a target word contained in a clinical description. Once a keyword is found, the processor deems that the clinical description does (or does not, as the case may be) relate to a treatment in which an adverse event has occurred. In some embodiments of the present disclosure, a flag is written to a header in the clinical description text file. By searching for a keyword in the text of a clinical description, training of a machine learning algorithm (involving training data) is not required, thereby freeing up system resources of a computing apparatus. The keyword search nature of the method and system of the present disclosure does not monopolize the processor of a computing apparatus performing the analysis of the clinical descriptions.

Figure 1:
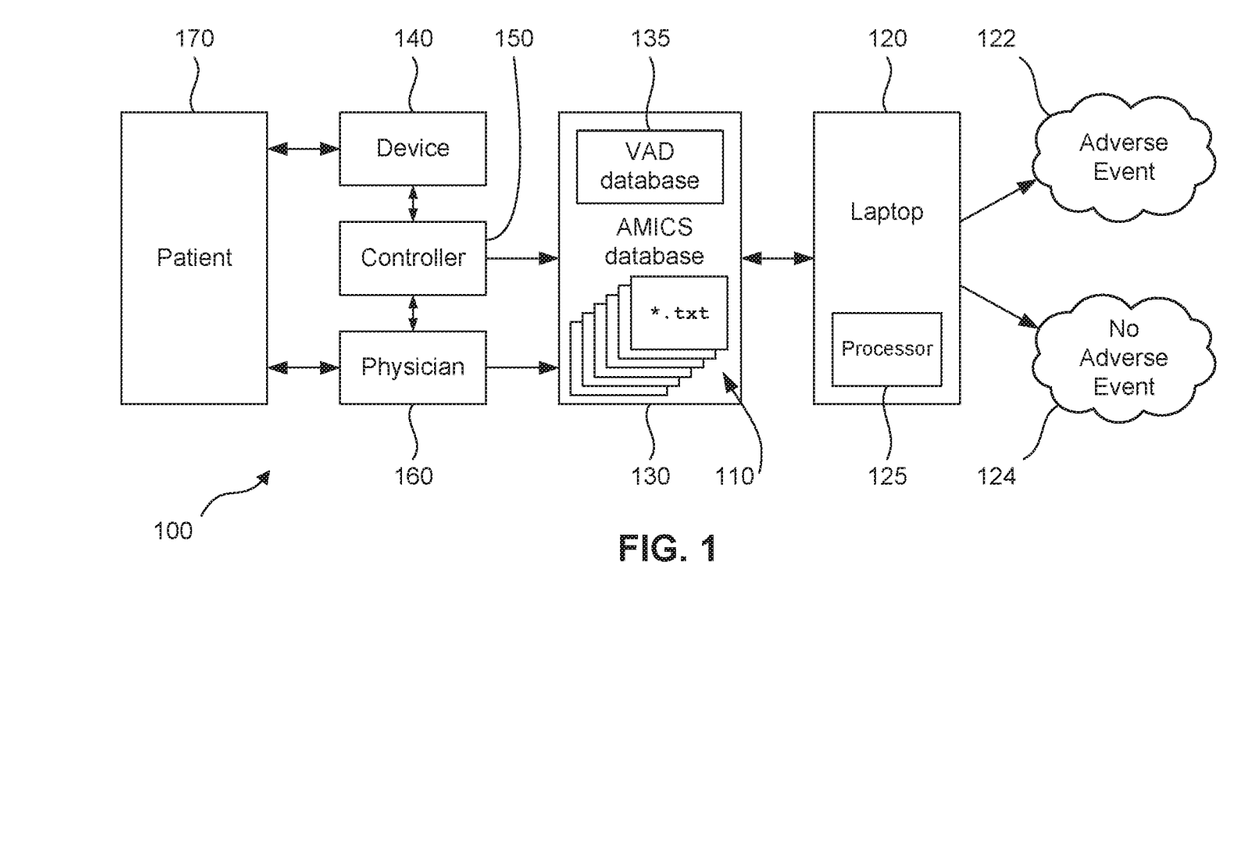
FIG. 1 shows an illustrative system for finding adverse events in a clinical description according to an embodiment of the present disclosure.

FIG. 1 illustrates a block diagram of a system 100 for automatically detecting the occurrence of adverse events in clinical descriptions 110. The system 100 comprises a computing apparatus 120, such as a laptop, for example, in communication with a patient data repository 130. For the sake of brevity only a processor 125 of the computing apparatus 120 is shown in FIG. 1. However it will be understood that computing apparatus 120 also comprises other components typically associated with a computing apparatus, such as, for example, a volatile memory (e.g. a random access memory RAM), a non-volatile memory (e.g. a read only memory ROM), a display, and connection busses that enable communication between these components, all of which are included in the present disclosure.

The computing apparatus 120 comprises a processor 125 which is able to execute machine readable instructions to perform operations on text data using natural language processing. The computing apparatus 120 is in communication with a patient data repository 130 comprising patient data obtained from various medical institutions. According to certain embodiments of the present disclosure, patient data repository 130 may comprise an Acute Myocardial Infarction Cardiogenic Shock (AMICS) database compiled and maintained by a CRM such as Salesforce.com, Inc. The AMICS database 130 stores data from treatment of high risk percutaneous coronary intervention (PCI) patients and patients in cardiogenic shock. The AMICS database 130 may also store data specific to the VADs 140 available for treatment in a VAD database 135. The VAD database 135 may comprise operational parameters for each device.

Patient data includes clinical descriptions 110 that have been stored in the AMICS database 130 after treatment of a patient in cardiogenic shock. Such treatment includes the use of a medical device to alleviate the patient's condition, such as, for example, a VAD 140. VADs provide ventricular support to a patient in cardiogenic shock and may comprise, but are not limited to, an Impella® pump, an Extracorporeal Membrane Oxygenation (ECMO) pump, a balloon pump, and a Swan-Ganz catheter. The Impella® pump may comprise an Impella 2.5® pump, an Impella 5.0® pump, an Impella CP® pump and an Impella LD® pump, all of which are by Abiomed, Inc. of Danvers, Mass.

VAD 140 is connected to a controller 150 which enables a physician 160 to operate the VAD 140 when treating the patient 170. Such operation may include navigating the VAD within the patient 170 and adjustment of operational parameters of the VAD 140 to suit the condition of the patient 170. Operational parameters include, but are not limited to, purge volume, flow rate, and pump speed, for example. According to certain embodiments of the present disclosure, the controller 150 may comprise an Automated Impella® Controller (AIC) by Abiomed, Inc. of Danvers, Mass.

Each VAD 140 may comprise at least one sensor that collects data from the patient 170 while the VAD is in use treating the patient. The patient data is transmitted as signals to the controller 150. Such data may include, but is not limited to, Mean Arterial Pressure (MAP), Left Ventricular Pressure (LVP), Left Ventricular End-Diastolic Pressure (LVEDP), Pulmonary Arterial Wedge Pressure (PAWP), Pulmonary Capillary Wedge Pressure (PCWP), and Pulmonary Artery Occlusion Pressure (PAOP). The controller 150 communicates the patient data to the AMICS database 130 which stores the data for analysis after the treatment. The AMICS database 130 may also be provided with additional data from the physician 160 (e.g. notes from treating the patient) that may be stored together with the patient data.

Data from the patient and physician may be stored as clinical descriptions 110 in the repository 130. In certain embodiments of the present disclosure, the clinical descriptions 110 may be stored in the AMICS database 130 in at least one text file having a *.txt extension. The clinical descriptions 110 may comprise text in any language (e.g. English) and/or shorthand (e.g. clinical shorthand). An illustrative clinical description is shown in Table 1. The text file may also include header information that contains identifying data such as, for example, name of the patient and medical institution, patient demographics, date, time (not shown in Table 1). It will be understood that the above are exemplary embodiments of the clinical descriptions, and that the term 'clinical description' encompasses any group of machine readable characters containing information that relates to a medical procedure performed on the patient, such as cardiovascular treatment using VADs.

TABLE 1

Illustrative clinical description in *.txt format.

Description: Cardiac Arrest patient with history of heart failure and CABG. Currently on Neo, Levo and unconfirmed amount of Epi. Patient was down and CPR performed by EMT and bystander prior to EMT arrival. Patient is awake and alert although intubated. Patient is on P6 with flows of 2.6 L/min. little difference in flows between P6 and P8 as patient is fairly constricted peripherally. Plan to wean Epi and Levo as soon as possible. Waiting for central line or Swan to be placed for assessment. He is currently getting volume at around 300 per hour. Watching output and have discussed potentially giving Lasix but will watch volume status for Impella. Have given bolus of 500 for volume after echo. Pressure is 91/76/80. PP is 602. purge flow is 11.2. MC at 619/489/546. groin site is dry with no evidence of bleeding at all. 10-24 parameters remain steady. Dialysis was started this morning at 7 am. MAP in the 70's with narrow pulse pressure. Patient is still alert and aware but lightly sedated. Patient passed last night The clinical descriptions 110 are assessed by the computing apparatus 120 for classification of various events that occur during the respective treatments. Events may include the occurrence of adverse events, malfunction of treatment devices, and success of a treatment, for example. Clinical descriptions 110 may be selected based on a specified set of criteria, such as, for example, geographical region, period of time, diagnosis type, patient age, and type of treatment device used (e.g. a VAD consisting of an Impella® CP pump). Such criteria may be predetermined or input by a clinician operating the laptop 120 via a graphical user interface (GUI), for example. Each selected clinical description 110 is then analyzed by the processor 125 of the computing apparatus 120 using a natural language processing (NLP) algorithm implemented by software. Examples of NLP software include, but are not limited to, Apache OpenNPL, Mallet, ELIZA and cTAKES.

The natural language processing algorithm determines if a keyword in each selected clinical description 110 is present. The keyword may comprise at least one word that acts on, or in relation to, a target word in the clinical descriptions 110. The keyword may be used to classify the selection of clinical descriptions 110. According to an embodiment of the present disclosure, the target word may be used to describe an adverse event that has occurred during treatment of the heart of the patient (e.g. bleeding, hemolysis or ischemia). Examples of target words may include 'bleed', 'clot', and 'heart', and examples of keywords may include 'not', 'non' and 'no'. Such keywords and target words may be predetermined and stored in a memory of the computing apparatus 120 for a specific type of analysis. Alternatively, the keywords and target words may be input by a clinician operating the computing apparatus 120 via a GUI of the NLP software. The occurrence of the keyword in an active region surrounding the target word is then analyzed by the NLP to determine if a particular event has occurred during the respective treatments. For example, the NPL may identify the occurrence of adverse events and flag a clinical description 110 as containing an adverse event 122, or not containing an adverse event 124.

Figure 2:
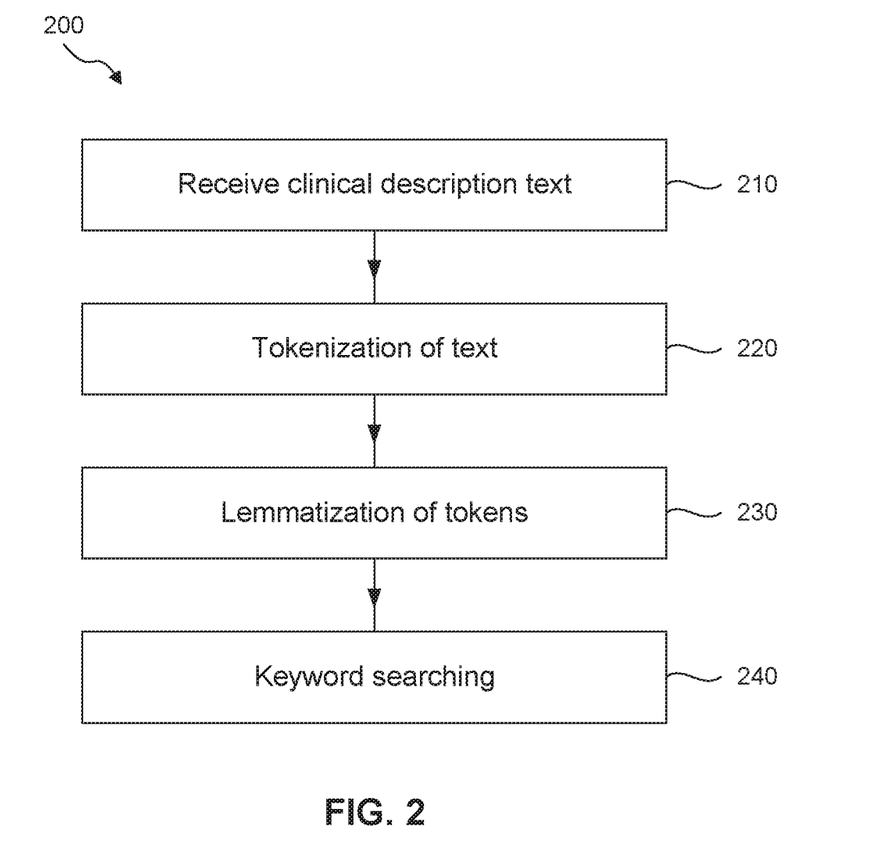
FIG. 2 shows an illustrative flowchart of a method of keyword searching used natural language processing.

FIG. 2 illustrates a flow chart representing a method 200 of natural language processing according to an embodiment of the present disclosure. The method 200 in FIG. 2 is carried out by the processor 125 in FIG. 1. The method begins at step 210 in which the processor 125 of the computing apparatus 120 obtains a selection of clinical descriptions 110 from the AMICS database 130. As previously mentioned, the selection of clinical descriptions 110 may be based on a specified set of criteria, such as, for example, geographical region, period of time, diagnosis type, patient age, and type of treatment device used (e.g. VAD). In step 220, the NPL algorithm splits the text of each clinical description 110 into pieces or tokens, termed tokenization of the text. Depending on the NPL algorithm used, certain characters in the text, such as punctuation characters, may be disregarded. Each token is used as a semantic unit for processing of the text associated with the selected clinical descriptions.

After tokenization of text, the method 200 then progresses to step 230, also known as lemmatization, in which similar tokens are grouped together based on inflected forms of a token so they can be analyzed as a single item. Essentially lemmatization (or stemming) links tokens having the same base form (root word) and groups them together so that the tokens can be treated in a similar manner. For example, in English, the verb 'to walk' may appear as 'walk', 'walked', 'walks', 'walking'. The base form here is 'walk', which one might look up in a dictionary. The output of the lemmatization step 230 is a bag-of-words (BOW) comprising groups of tokens, each group having an associated base form.

Once a BOW is formed for the selected clinical description 110, keyword searching can take place (step 240). The NPL lemmatizes the target word and identifies the root word of the target word. Next the NPL scans the BOW to determine if the root word of the target word occurs in the BOW. If such a determination is positive, i.e. if the BOW contains a root word that matches that of the target word, the selected clinical description 110 is deemed to contain the target word. Conversely, if the determination is negative, i.e. if the BOW does not contain the root word of the target word, the selected clinical description 110 is deemed not to contain the target word.

Figure 3:
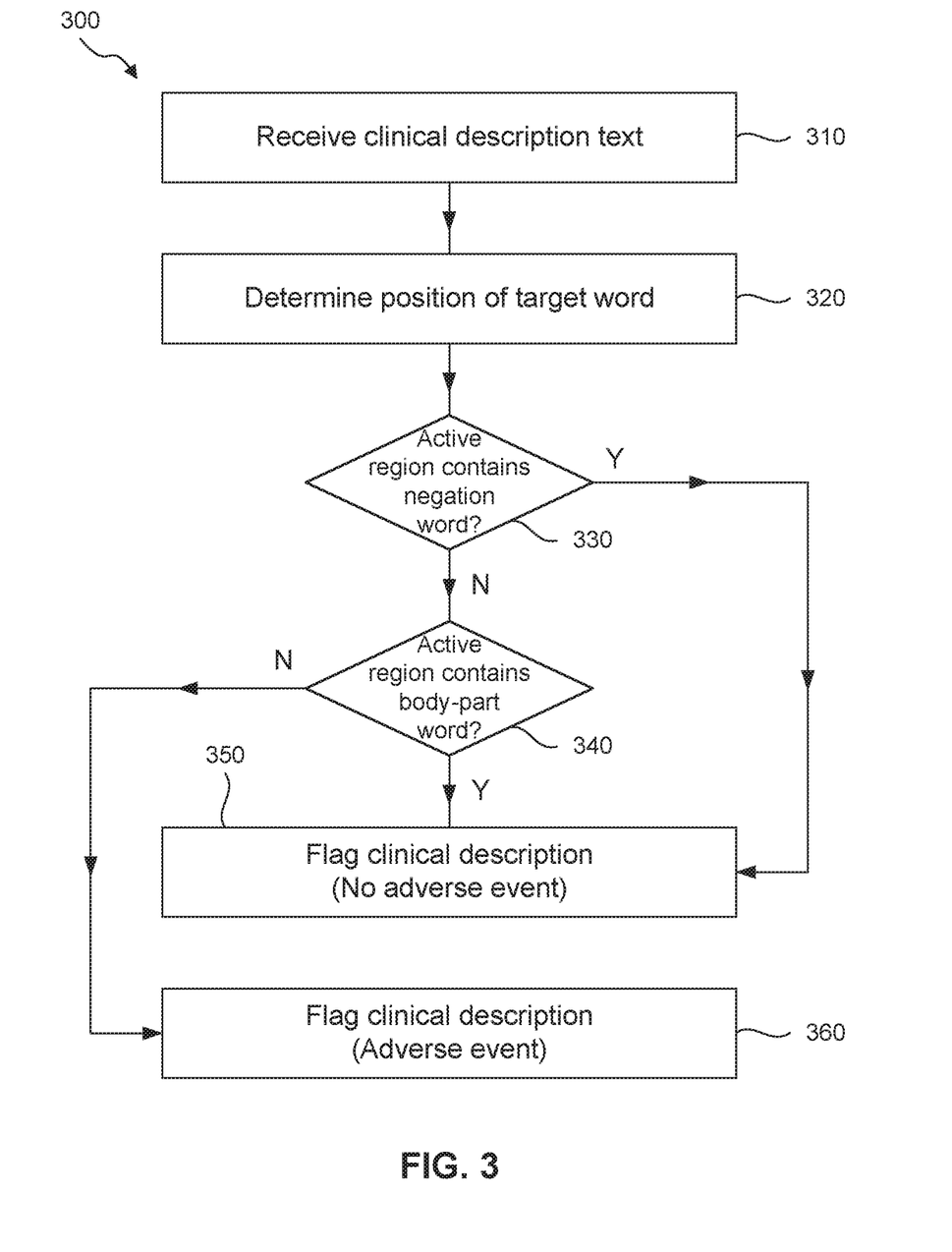
FIG. 3 shows an illustrative flowchart of a method of finding adverse events in a clinical description according to an embodiment of the present disclosure.

FIG. 3 shows a flow diagram of a method 300 for automatically classifying clinical descriptions 110 according to an embodiment of the present disclosure. The method 300 in FIG. 3 is carried out by the processor 125 in FIG. 1. As with the method 200, the method 300 begins at step 310 in which the processor 125 of the computing apparatus 120 obtains a selection of clinical descriptions 110 from the AMICS database 130. As previously mentioned, the selection of clinical descriptions 110 may be based on a specified set of criteria, such as, for example, geographical region, period of time, diagnosis type, patient age, and type of treatment device used (e.g. VAD). The criteria may be specified by the clinician via a GUI of the computing apparatus 120.

In step 320, the processor 125 uses the NPL algorithm running thereon to determine the position of a target word in each selected clinical description 110. Once the position of the target word is identified, the method 300 additionally uses the NPL process 200 to further identify an active region in relation to the target word. The active region comprises a predetermined number of words within the text of the selected clinical description 110 occurring immediately before and immediately after the target word. The active region also includes the target word. The predetermined number of words may be stored within the computing apparatus 120, or may be provided as an input from the clinician via a GUI. The predetermined number of words defines the size of the active region (i.e. the granularity of the method 300), and will be termed henceforth the granularity size.

The method 300 then proceeds to analyze the active region in each selected clinical description 110. Here the processor 125 searches the active region in each of the selected clinical descriptions 110 for a keyword using the NPL method 200. As described in the foregoing, the keyword acts on, or in relation to, the target word in each clinical description 110. According to embodiments of the present disclosure, the keyword may comprise a negation word or a body-part word. A negation word may comprise, but is not limited to, 'no', 'not', 'nor', 'non', 'without', 'never', and 'false'. The presence of a negation word in the active region of a target word reverses or deactivates the ordinary meaning of the target word. For example, if the clinical description reads " . . . groin site is dry with no evidence of bleeding at all . . . ," the presence of the negation word 'no' deactivates the meaning of the target word 'bleeding' occurring at that the groin site. Thus upon detecting the negation word 'no' in the active region, the processor 125 would flag this clinical description as not relating to an adverse event, the adverse event being bleeding in the groin.

In a similar manner, a body-part word may comprise any body part such as, for example, 'leg', 'arm', 'abdomen' and 'groin'. The presence of a body-part word in the active region of a target word deactivates the ordinary meaning of the target word. Unlike the negation word, according to an embodiment of the present disclosure, the presence of a body-part word signifies that the adverse event (for example bleeding) does not occur in the heart. For example, if the clinical description reads " . . . patient is very sick and they feel she is bleeding into her abdomen . . . ," the presence of the body-part word 'abdomen' deactivates the meaning of the target word 'bleeding' as it does not relate to the heart. According to an embodiment of the present disclosure, it will be assumed that any adverse event in a clinical description that does not have a body-part word acting on a target word occurs in the heart of a patient. Thus upon detecting the body-part word 'abdomen' in the active region, the processor 125 would flag this clinical description as not relating to the adverse event of bleeding in the heart. It will be understood that the NPL keyword search could be customized further to match words in the active region to a specific body-part word, e.g. 'heart', and flag the clinical description based on a match.

Referring back to FIG. 3, once the position of the target word in the text of a clinical description 110 is determined, method 300 proceeds to step 330 where it is further determined if a negation word is present in the active region. If a negation word is present in the active region (Yes' in step 330), the clinical description is flagged as not containing an adverse event. In certain embodiments of the present disclosure, the flag may be written in the header of the text file for each clinical description (in ASCII characters, for example), and the flagged clinical description 110 may be written back to the AMICS database by the computing apparatus 120.

If a negation word is not present in the active region ('No' in step 330), the method 300 proceeds to step 340 where it is further determined if a body-part word is present in the active region. If a body-part word is present (Yes' in step 340), the clinical description is flagged as not containing an adverse event, as in step 350. If a body-part word is not present (No' in step 340), the clinical description is flagged as containing an adverse event, as in step 360. In certain embodiments of the present disclosure, the flag in both cases of 'Yes' and 'No' to step 340 may be stored in the header of the text file for each clinical description, and the flagged clinical description 110 may be written back to the AMICS database by the computing apparatus 120.

The strategic keyword searching of the present disclosure scans text within each clinical description 110 to locate the target word and any specified keywords within an active region of the target word. Once a keyword is identified, the clinical description is flagged and the analysis moves on to the next text file. This places no burden on the processor compared to NPL using machine learning, and therefore frees up the processing power of the computing apparatus.

Figure 4:
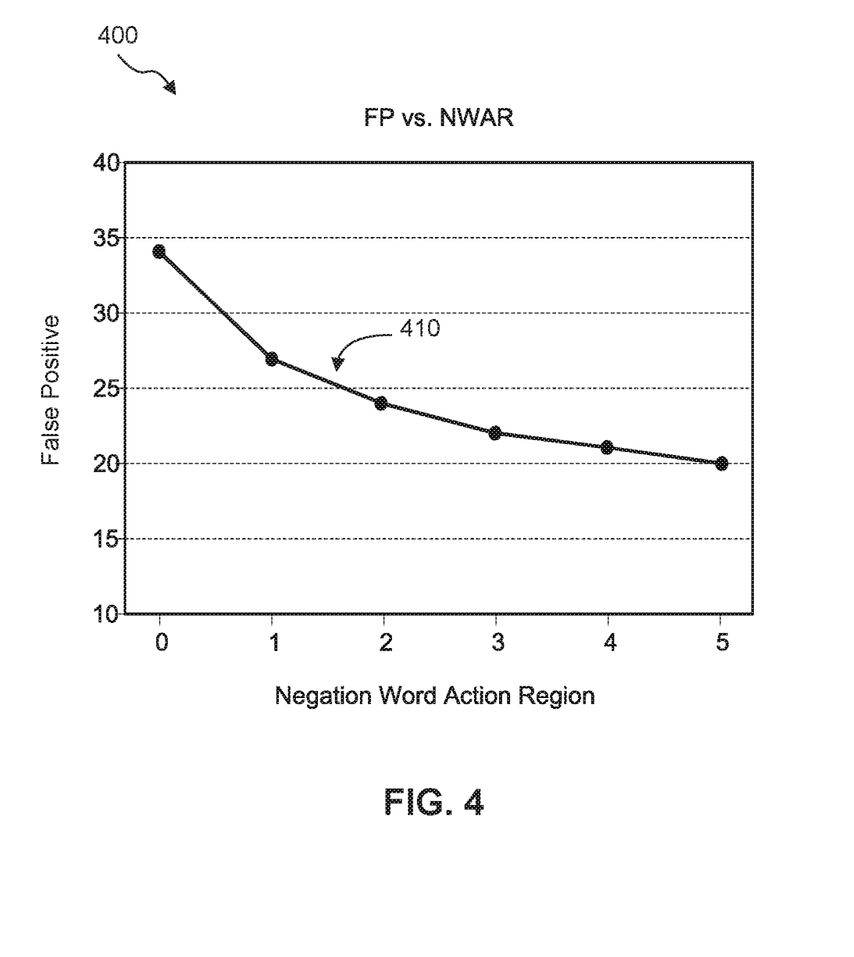
FIG. 4 illustrates optimization of the length of an action region surrounding a target word in relation to the number of false positives that arise using the method of FIG. 1.

FIG. 4 shows optimization chart 400 of the NPL algorithm based on the size of an active region for detecting a negation word with respect to a target word, in accordance with an embodiment of the present disclosure. In effect this optimizes the granularity of the method 300. As previously described, the number of false positives (FP) refers to the number of times the processor 125 does not detect the presence of a negation or body-part word in an active region when the negation or body-part word is actually present, whiletrue positive, TP, means the negation or body-part words are there and also detected. In effect the FP is a missed alarm as the processor 125 misses the detection of a bleeding event in the heart of the patient, according to the clinical description 110, by incorrectly identifying a negation or body-part word in the active region of a clinical description. Similarly, the number of false negatives (FN) refers to the number of times the processor 125 incorrectly detects the presence of a negation or body-part word in an active region when there is no negation or body-part word actually present, wheretrue negative, TN, means no negation or body-part words existed or detected.

In FIG. 4, the size of the active region is referenced with respect to the number of words immediately before and immediately after a target word. The optimization is performed with respect the number of false positives. The line plot 410 in the optimization chart 400 shows that the occurrence of false positives shows minimal variation with active regions having a granularity of three words or more. Further, Table 2 shows exemplary values of TP, FP, FN and TN as the granularity of the active region changes. The values in Table 2 reinforce the trend shown in FIG. 4 where the number of missed alarms, i.e. FP, is reduced as the size of the active region increases. The rate of reduction of FP plateaus after a critical granularity of the active region. According to embodiments of the present description, the critical size of the active region is taken as three words.

TABLE 2

Optimization of FP with size of active region.

| Active Region | Prediction | TP | FP | FN | TN |
|---|---|---|---|---|---|
| 0 | 73 | 39 | 34 | 1 | 346 |
| 1 | 66 | 39 | 27 | 1 | 353 |

TABLE 2-continued

Optimization of FP with size of active region.

| Active Region | Prediction | TP | FP | FN | TN |
|---|---|---|---|---|---|
| 2 | 63 | 39 | 24 | 1 | 356 |
| 3 | 61 | 39 | 22 | 1 | 358 |
| 4 | 60 | 39 | 21 | 1 | 359 |
| 5 | 59 | 39 | 20 | 1 | 360 |

Figure 5A:
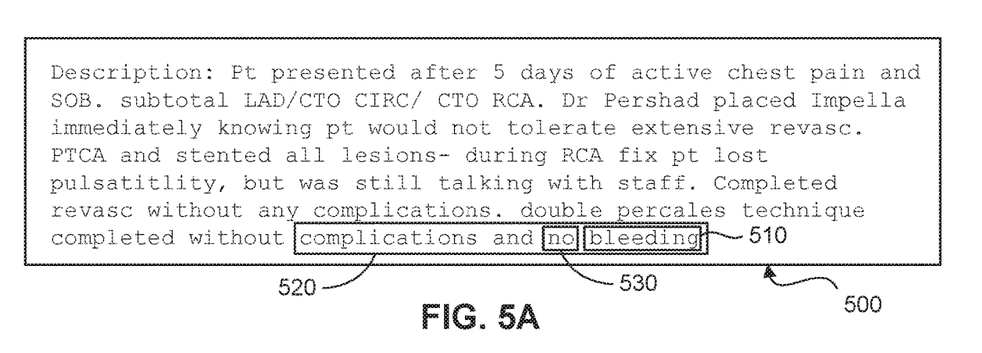
FIGS. 5A and 5B illustrate the use of the method of FIG. 1 on a clinical description containing a negation word.
Figure 5B:
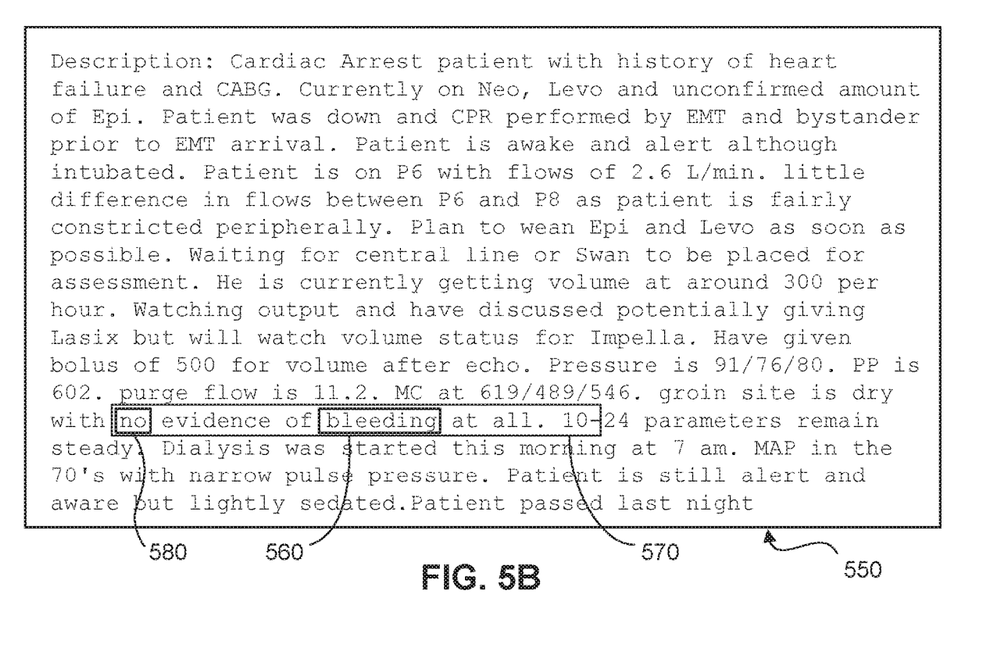

FIGS. 5A and 5B illustrates examples of using an NPL algorithm to automatically detect the presence of a negation word in clinical descriptions 500, 550, according to the systems and methods as described in the foregoing. In FIG. 5A, the target word 510 is 'bleeding', and the active region 520 has a granularity of three. The keyword 530 is a negation word 'no'. As the negation word 530 occurs within the active region 520 of the target word 510, the clinical description 500 is flagged as not containing an adverse event. Similarly, in FIG. 5B, the target word 560 is 'bleeding', and the active region 570 has a granularity of three. The keyword 580 is a negation word 'no'. As the negation word 580 occurs within the active region 570 of the target word 560, the clinical description 550 is flagged as not containing an adverse event. In both examples above, NPL processing according to the method 200 shown in FIG. 2 is used to identify the target word, the negation word and the words in the active region.

FIGS. 6A and 6B illustrates examples of using an NPL algorithm to automatically detect the presence of a body-part word in clinical descriptions 600, 650, according to the systems and methods as described in the foregoing. In FIG. 6A, the target word 610 is 'bleeding', and the active region 620 has a granularity of three. The keyword 630 is a body-part word 'abdomen'. As the body-part word 630 occurs within the active region 620 of the target word 610, the clinical description 600 is flagged as not containing an adverse event. As previously described, it is assumed that any adverse event in a clinical description that does not have a body-part word acting on a target word occurs in the heart of a patient. Thus upon detecting the body-part word 'abdomen' in the active region 620, the processor 125 flags the clinical description 600 as not relating to the adverse event of bleeding in the heart. Similarly, in FIG. 6B, the target word 660 is 'bleeding', and the active region 670 has a granularity of three. The keyword 680 is the body-part word 'groin'. As the body-part word 680 occurs within the active region 670 of the target word 660, the clinical description 650 is flagged as not containing an adverse event. In both examples above, NPL processing according to the method 200 shown in FIG. 2 is used to identify the target word, the body-part word and the words in the active region.

Table 3 shows a confusion matrix which provides exemplary figures to illustrate the effectiveness of the methods and systems of the present disclosure. Table 3 compares the results of using NPL to perform a complete keyword search using NPL on every word in a clinical description against the strategic negation and/or body-part keyword search using NPL to search for just the negation and/or body-part words in an active region of a target word according to embodiments of the present disclosure. Indices that are relevant to confusion matrices include ratios for precision, recall and accuracy. The precision ratio is determined using the formulation: TP/(TP+FP); the recall ratio is determined using the formulation: TP/(TP+FN); and the accuracy ratio is determined using the formulation: (TP+TN)/(TP+FP+FN+TN). For the illustrative confusion matrix of Table 3, the precision, recall and accuracy indices for the complete keyword search are 53.4%, 97.5% and 91.7%, respectively, whereas the same indices for the strategic negation and/or body-part keyword search are 74.0%, 92.5% and 96.2%, respectively. These comparative indices show that the strategic negation and/or body-part keyword search identifies keywords with a higher precision and accuracy. Such figures are indicative that the strategic negation and/or body-part keyword search of the present disclosure is superior over conventional NPL techniques, while minimizing the use of system resources to perform such natural language processing.

As previously described, after each selected clinical description 110 is flagged, the flag may be stored in the header of each clinical description text file, and the text file may be written back to the AMICS database 130 by the computing apparatus 120. To that end, a clinician may be able to filter flagged clinical descriptions from the AMICS database based on certain criteria (e.g. VAD type, patient age, name of medical institution) to obtain the percentage of clinical descriptions that contain a target word. For example, a clinician operating the computing apparatus 120 may be able to obtain data from the AMICS database relating to the Impella® 2.5 heart pump used on male patients aged 50-55 years old in Boston, Mass. that suffered from bleeding in the heart during a cardiac procedure. If such data is below what has been statistically shown for patients matching the criteria, it could be indicative of various issues. Such issues may include, for example, that the cardiac procedure is administered to the patient incorrectly, or that the VAD used has faults that need to be rectified. In the case of incorrect administration of a cardiac procedure, such data could initiate further training at medical institutions. In the case of suspected faults in the VAD, such data can be used as quality control during manufacture of such devices. Further, the data obtained from flagged clinical descriptions containing adverse events may be used to trigger a lock-out mechanism to warn the physician against the use of the use of a VAD, if the number of flagged clinical descriptions exceeds a predetermined threshold. Thus flagging clinical descriptions in an automatic manner as described in the foregoing will be able to provide clinicians with feedback that could improve the treatment provided to the patient.

TABLE 3

Confusion matrix comparison.

| | Real Positive | Real Negative | Total |
|---|---|---|---|
| COMPLETE KEYWORD SEARCH | | | |
| Predict Positive | TP = 39 | FP = 34 | 73 |
| Predict Negative | FN = 1 | TN = 346 | 347 |
| Total | 40 | 380 | 420 |
| NEGATION/BODY-PART KEYWORD SEARCH | | | |
| Predict Positive | TP = 37 | FP = 13 | 50 |
| Predict Negative | FN = 3 | TN = 367 | 370 |
| Total | 40 | 380 | 420 |

The foregoing is merely illustrative of the principles of the disclosure, and the apparatuses can be practiced by other than the described implementations, which are presented for purposes of illustration and not of limitation. It is to be understood that the methods disclosed herein, while shown for use in automated ventricular assistance systems, may be applied to systems to be used in other automated medical systems.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A method for automatically classifying clinical descriptions of patients, the method comprising:
   receiving, with one or more processors, at least one clinical description file from a data repository comprising a plurality of clinical description files, wherein each clinical description file comprises text relating to the use of a ventricular assist device (VAD) on a corresponding patient;
   determining, with the one or more processors, a position of a target word within the text of the at least one clinical description file;
   determining, with the one or more processors, whether at least one of a plurality of predetermined negation words is located within an active region, wherein the active region comprises the target word and a predetermined number of words within the text occurring immediately before and immediately after the target word;
   determining, with the one or more processors, whether at least one of a plurality of predetermined body-part words is located within the active region; and
   writing, with the one or more processors, a flag to a header of the at least one clinical description file in response to a determination that the active region does not contain at least one of the plurality of predetermined negation words or at least one of the plurality of predetermined body-part words, wherein the flag indicates that the at least one clinical description file contains an adverse event.

2. The method of claim 1, wherein determining the position of the target word comprises:
   processing the text of the at least one clinical description file to generate word tokens;
   determining and grouping word tokens comprising inflected forms of a word; and
   performing a keyword search on the text using the grouped word tokens.

3. The method of claim 1, wherein the predetermined number of words of the active regions is at least three words.

4. The method of claim 3, wherein the predetermined number of words of the active regions is three words.

5. The method of claim 1, wherein the plurality of predetermined negation words are selected from 'no', 'not', 'nor', 'non', 'without', 'never', or 'false'.

6. The method of claim 1, wherein the data repository is an Acute Myocardial Infarction Cardiogenic Shock (AM-ICS) repository.

7. The method of claim 1 further comprising:
   disabling, with the one or more processors, the use of at least one VAD in response to a determination that the number of clinical description files containing adverse events exceeds a predetermined threshold.

8. The method of claim 1 further comprising:
   initiating, with the one or more processors, further training at a medical institution in response to a determination that the number of clinical description files containing adverse events exceeds a predetermined threshold.

9. The method of claim 1 further comprising:
   initiating, with the one or more processors, manufacturing quality control procedures in response to a determination that the number of clinical description files containing adverse events exceeds a predetermined threshold.

10. The method of claim 1, wherein the target word is 'bleed', 'clot', or 'heart'.

11. The method of claim 10, wherein the plurality of predetermined body-part words are selected from 'leg', 'arm', 'abdomen', or 'groin'.

12. The method of claim 11, wherein the plurality of predetermined negation words are selected from 'no', 'not', 'nor', 'non', 'without', 'never', or 'false'.

13. The method of claim 1, wherein the target word is 'bleed', wherein at least one of the plurality of predetermined negation words is 'no', and wherein the plurality of predetermined body-part words are selected from 'leg', 'arm', 'abdomen', and 'groin'.

14. A system for automatically classifying clinical descriptions of patients, the system comprising:
   a data repository comprising a plurality of clinical description files, wherein each clinical description file comprises text relating to the use of a ventricular assist device (VAD) on a corresponding patient; and
   one or more processors in communication with the data repository and configured to:
      receive at least one of the clinical description files;
      determine a position of a target word within the text of the at least one clinical description file;
      determine whether at least one of a plurality of predetermined negation words is located within an active region, wherein the active region comprises the target word and a predetermined number of words within the text occurring immediately before and immediately after the target word;
      determine whether at least one of a plurality of predetermined body-part words is located within the active region; and
      write a flag to a header of the at least one clinical description file in response to a determination that the active region does not contain at least one of the plurality of predetermined negation words or at least one of the plurality of predetermined body-part words, wherein the flag indicates that the at least one clinical description file contains an adverse event.

15. The system of claim 11 further comprising:
   at least one VAD for treating a patient; and
   a controller in communication with the VAD and the data repository,
   wherein the controller is configured to communicate patient data from the at least one VAD to the data repository, and
   wherein the data repository is configured to store a clinical description file comprising the patient data from the at least one VAD.

16. The system of claim 15, wherein the one or more processors are further configured to disable the use of the at least one VAD in response to a determination that the number of clinical description files containing adverse events exceeds a predetermined threshold.

17. A non-transitory computer readable storage medium having instructions stored thereon, which, when executed by one or more processors, cause the one or more processors to:

receive at least one clinical description file from a data repository comprising a plurality of clinical description files, wherein each clinical description file comprises text relating to the use of a ventricular assist device (VAD) on a corresponding patient;

determine a position of a target word within the text of the at least one clinical description file;

determine whether at least one of a plurality of predetermined negation words is located within an active region, wherein the active region comprises the target word and a predetermined number of words within the text occurring immediately before and immediately after the target word;

determine whether at least one of a plurality of predetermined body-part words is located within the active region; and write a flag to a header of the at least one clinical description file in response to a determination that the active region does not contain at least one of the plurality of predetermined negation words or at least one of the plurality of predetermined body-part words, wherein the flag indicates that the at least one clinical description file contains an adverse event.

18. The system of claim 14, wherein the one or more processors are further configured to disable the use of at least one VAD in response to a determination that the number of clinical description files containing adverse events exceeds a predetermined threshold.

* * * * *

UNITED STATES PATENT AND TRADEMARK OFFICE
CERTIFICATE OF CORRECTION

| | |
|---|---|
| PATENT NO. | : 11,521,723 B2 |
| APPLICATION NO. | : 16/722303 |
| DATED | : December 6, 2022 |
| INVENTOR(S) | : Chen Liu et al. |

Page 1 of 1

It is certified that error appears in the above-identified patent and that said Letters Patent is hereby corrected as shown below:

In the Specification

Column 7, Line 60:
Now reads: "(Yes"; should read –('Yes'–

Column 8, Line 4:
Now reads: "(Yes"; should read –('Yes'–

Column 8, Line 7:
Now reads: "(No"; should read –('No'–

In the Claims

Column 12, Claim 15, Line 58:
Now reads: "11"; should read –14–

Signed and Sealed this
Twenty-first Day of February, 2023

Katherine Kelly Vidal
*Director of the United States Patent and Trademark Office*